United States Patent [19]
Okamoto et al.

[11] 4,273,811
[45] Jun. 16, 1981

[54] METHOD OF APPLYING SLIP TO INTERIOR SURFACES OF A CLOSED TANK TO PROVIDE AN ENAMEL COATING

[75] Inventors: Joji Okamoto; Hitoshi Azuma; Katsushi Arai; Takemi Naito, all of Yanai; Seiji Kawai, Yamaguchi; Minoru Goto, Hitachi, all of Japan

[73] Assignee: Hitachi, Ltd., Tokyo, Japan

[21] Appl. No.: 836,951

[22] Filed: Sep. 27, 1977

[30] Foreign Application Priority Data

Oct. 8, 1976 [JP] Japan .............................. 51-120357

[51] Int. Cl.[3] ............................................ G01N 33/02
[52] U.S. Cl. .................................... 427/232; 118/408; 427/234; 427/238
[58] Field of Search ............... 427/231, 238, 232, 234; 118/55, 408

[56] References Cited

U.S. PATENT DOCUMENTS

| | | | |
|---|---|---|---|
| Re. 24,187 | 7/1956 | Burwell | 118/55 |
| 2,121,404 | 6/1938 | O'Neil | 427/232 |
| 3,376,152 | 4/1968 | Okamoto | 427/232 |

FOREIGN PATENT DOCUMENTS

| | | | |
|---|---|---|---|
| 552321 | 6/1932 | Fed. Rep. of Germany | 427/232 |
| 2411881 | 9/1975 | Fed. Rep. of Germany | 427/232 |

*Primary Examiner*—Sam Silverberg
*Attorney, Agent, or Firm*—Craig and Antonelli

[57] ABSTRACT

A method whereby slip is applied for providing an enamel coating to interior surfaces of a tank such as a heat exchanger of a hot water boiler, electric water heater and the like fabricated beforehand as by welding. In this method, a larger amount of slip than that actually required for applying the slip coating to the interior surfaces of the tank is introduced into the tank to be applied thereto with the tank being rotated, and the excess slip which has not been applied to the surfaces is forcedly drained from the tank at a rate higher than the rate at which the slip moves relative to the enameled surfaces and which moving rate is determined by the liquid level of the slip within the tank and the size of a discharge port, so that an enamel coating of a desired thickness can be formed on the interior surfaces of the tank. In order to forcedly drain the excess slip from the tank, pneumatic pressure is supplied to the interior of the tank prior to slip application. The particle size, specific gravity and drying means for the slip are disclosed herein.

16 Claims, 7 Drawing Figures

METHOD OF APPLYING SLIP TO INTERIOR SURFACES OF A CLOSED TANK TO PROVIDE AN ENAMEL COATING

List of Prior Art Reference (37 CFR 1.56(a))
The International Enamelist 17[4] 3–6.
"New line porcelain enamels water heaters"

BACKGROUND OF THE INVENTION

This invention relates to a method of applying slip for an enamel coating to interior surfaces of a tank such as a heat exchanger of a hot water boiler, electric water heater, hot water storage tank, etc., and more particularly to a method of applying the slip to the interior surfaces of a tank after it is fabricated as by welding. Specifically, the invention is directed to the provision of a heat exchanger of a hot water boiler with a hot water resisting enamel coating.

In this specification, the term "closed tank" refers to such a tank that has openings, such as nipples, of which areas are small as compared with the internal volume of the tank, and a closed tank is hereinafter referred to as a tank. Also, porcelain enameling is a general term for both porcelain enameling and glass lining.

In the prior art porcelain enameling processes, slip is applied to various components of the tank by spraying before they are assembled into a tank, and the components are baked and assembled together by welding to provide an enameled tank.

According to the prior art processes, it is possible to provide an enamel coating of a desired film thickness, and defects in an enamel coating can be readily detected because enamel application is separately effected for each component of the tank. Thus the component with defects in enamel coating can be subjected to enamel application again. Therefore, these processes are now being used widely, but are disadvantageous in that manufacturing costs are high, as described hereinbelow. Since slip is applied by spraying, it scatters and its rate of recovery is low. Each part of the tank must be baked in a furnace. The parts of the tank must be relieved of enamel at such portions thereof to be welded. In addition, these processes have the following disadvantages. The portions of the parts which have been relieved of the enamel coating may become defective due to the fact that they tend to be brought into contact with the liquid in the tank because of misalignment which would arise when the parts are joined. A weld bead (backing bead) at the joints tends to be exposed. Also, when a tank is fabricated, one component is force fitted into another component and then is welded thereto. There is a danger of the enamel coating chipping off during force fitting.

As described above, the conventional method for enamel application requires that after slip application the various components of a tank be subject to force fitting and welding. Therefore, various problems have been encountered in carrying out this method.

In order to overcome these disadvantages, it has been proposed to perform slip application after a tank is fabricated, thereby eliminating force fitting and welding operations after porcelain enameling. When such measures are employed, it is essential that slip application be completely performed since it is impossible to inspect porcelain enameling over the interior surfaces of the closed tank from outside.

A proposal has been made to first fabricate a tank and then to apply slip by shooting wet slip through hoses into the tank so that 'flow coating' can be effected, as described in 'NEW LINE PORCELAIN ENAMELS WATER HEATERS' of 'THE INTERNATIONAL ENAMELIST', 17[4] pages 3 to 6, published October 1967. This method requires skills in carrying it into practice, and is not suitable for a tank having an inner shell and an outer shell, such as the tank of a hot water boiler.

It is considered likely that if slip of a smaller amount than the internal volume of a tank is introduced into the tank, the tank is rotated for effecting slip application and then excess slip that has not been used for slip application is drained from the tank, it will be possible to provide an enamel coating of a desired uniform thickness. However, the results of experiments show that it is impossible to provide an enamel coating of a desired uniform thickness by this method. Moreover, two problems are encountered in carrying out this method. One is that some surfaces of the tank are not substantially entirely coated with enamel, and the other is that the slip applied to the surfaces to form an enamel coating of a desired thickness tends to slump or sag, with the result that no enamel coating of a uniform thickness can be formed. In the aforementioned type of tank, it is generally believed that an enamel coating must have a thickness of over 120μ.

SUMMARY OF THE INVENTION

An object of this invention is to provide a method of applying slip to interior surfaces of a tank wherein a smaller amount of slip than the internal volume of the tank is introduced thereinto after the tank has been fabricated, and then the slip is applied thereto during rotation of the tank.

Another object is to provide a method of applying slip to a tank having a slip outlet port of a small size, so that one of the ports formed in the tank for connection with pipes can be utilized as a slip outlet port.

Another object of this invention is to provide a method of applying slip to a tank to provide an enamel coating formed of frits having hot water resistant characteristics.

Another object of this invention is to provide a method of applying slip to a tank to provide an enamel coating which is suitable for a tank of a heat exchanger of a hot water boiler.

Another object is to provide a method of applying slip which enables an enamel coating of a desired thickness to be provided by a single slip applying operation.

According to the invention, there is provided a method of applying slip to interior surfaces of a closed tank to provide an enamel coating thereon, comprising the steps of introducing into the closed tank slip of a larger amount than that actually required for application to the interior surfaces thereof and smaller than the interior volume of the tank, effecting slip application while the tank is being rotated, and forcedly draining excess slip from the tank.

DESCRIPTION OF PREFERRED EMBODIMENTS

Figure 1:
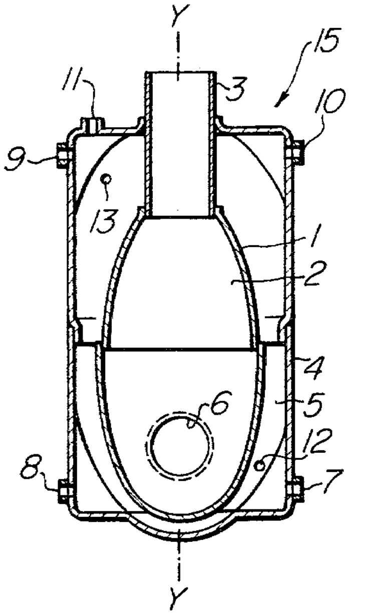
FIG. 1 is a vertical sectional view of a tank for a hot water boiler.

The method of applying slip for providing an enamel coating according to this invention consists of fabricating a tank, introducing into the tank slip of a smaller amount than the internal volume of the tank, and effecting slip application to interior surfaces of the tank while the tank is being rotated. The method according to the invention is characterized by effecting control of the rate at which excess slip is discharged or effecting forced draining of the excess slip from the tank, and by being able to provide an enamel coating of a uniform thickness by selecting suitable slip.

We have conducted a series of experiments which have revealed that when a conventional slip applying method is used, portions of the tank on which no slip is applied are those portions which are located below the liquid level of excess slip to be drained when rotation of the tank is stopped, and that portions of the tank which are located above the liquid level are formed with a coat of slip of a desired thickness. More specifically, interior surfaces of a tank are formed with a coat of slip of a desired thickness as the result of rotation of the tank, but since excess slip is drained from the tank under atmospheric pressure, the rate of movement of the liquid level of the excess slip relative to the slip applied surface at the time of draining of the excess slip is low. Because of this low rate of flow of the excess slip, the coat of slip applied to the interior surfaces of the tank is stripped off by surface tension when the excess slip is drained from the tank. Draining of the excess slip is done by gravity and the rate at which draining is effected depends on the size of the outlet ports and the height of the liquid level of the excess slip from the outlet ports. Generally, feedwater ports of a small diameter of the tank are utilized as the outlet ports for the excess slip, so that the rate of flow of the excess slip on the slip applied surfaces is low. Generally, when paint is applied by this method, it is known that the thickness of a coat of paint is related to the rate at which the painted surface is raised relative to the paint and is porportional to such rate. It is considered that the slip application shows the same phenomenon as the application of a paint, so that the coat of slip is reduced in thickness because of the fact that the speed at which excess slip flows is lower than that required for forming a coat of a required thickness.

The aforementioned phenomenon of sagging of the applied slip is considered to be related to the nature of the slip and the presence of cluster thereof.

According to the method of the invention, excess slip is forcedly drained from the tank to flow at a predetermined rate in order to eliminate any incomplete slip application. That is, the portion of the interior surfaces of the tank which is above the liquid level of the slip are applied with slip at the rotational speed of the tank and the portion of the interior surfaces of the tank which is below the liquid level of the slip is applied with slip at the same rate as that at which the slip is drained from the tank. Slumping and sagging of the slip can be prevented by selecting a suitable particle size for the slip and preventing cluster thereof.

Figure 2:
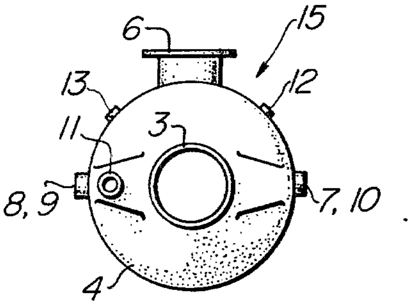
FIG. 2 is a plan view of the tank shown in FIG. 1.

One embodiment of the invention will now be described with reference to the accompanying drawings. Pressurized air for draining slip at a predetermined rate is utilized. FIGS. 1 and 2 show a tank 15 in which slip application is to be performed. The tank is used for a hot water boiler and comprises an inner shell 1 defining a combustion chamber 2 therein, an outer shell 4, and a flue 3 connected to an upper end of the combustion chamber 2. The outer shell 4 cooperates with the inner shell 1 to define therebetween a hot water reservoir 5. The inner and outer shells 1 and 4 respectively are formed by joining together by welding halves thereof which have been fabricated by press forming, and are substantially ellipsoidal shaped. The numeral 6 designates a cylindrical burner which extends transversely through the outer shell 4 from the inner shell 1. The numerals 7 and 8 designate feedwater ports mounted on the opposite sides of the water shell and the numerals 9 and 10 hot water outlets mounted on the opposite sides of the outer shell. One of the feedwater ports 7 serves as a port for discharging slip therethrough. The numeral 11 designates a hot water outlet positioned at the top of the tank, and the numerals 12 and 13 designate openings formed on the side of the tank for mounting therein electrodes for cathodic protection.

The various dimensions of the tank used in the experiments are as follows: the maximum diameter of the inner shell 1 is about 400 mm; the height of the inner shell 1 is about 830 mm; the outer diameter of flue 3 is about 160 mm; the maximum inner diameter of outer shell 4 is about 440 mm; and the height of outer shell 4 is about 1,030 mm. These parts are all formed of cold rolled steel sheets suitable for porcelain enameling. The internal volume of the tank is about 60 l; the inner diameters of the feedwater ports 7 and 8 and hot water outlets 9 to 11 respectively are 29 mm; and the inner diameters of electrode mounting openings 12 and 13 respectively are 10 mm. The tank is rotated at 20 rpm about an axis Y—Y of rotation shown in FIG. 1 during slip application, and the duration of time during which the tank is rotated is about 30 seconds. The pneumatic pressure (gage pressure) is 1.2 kg/cm$^2$, and the amount of slip introduced into the tank is 20 l. The nature of the slip used is as follows. A combination of three types of frits manufactured by Nippon Ferro Company and having hot water resistant characteristics was selected as slip for the experiments. The three types of frits were blended with one another according to the standard compounding process. The resulting slip has a specific gravity of 1.76, a viscosity cup time of 5.4 seconds (measures NK-2 type viscosity cup for paint manufactured by Iwata Painting Equipment Industry Company and reconstructed to have an outlet port having a diameter of 6.5 mm), a pickup value of 10 g/dm$^2$, and a particle size of 40 g.

Figure 3:
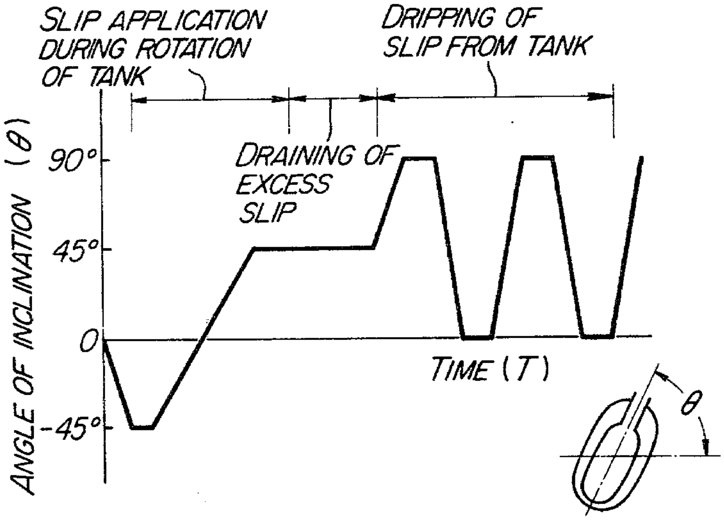
FIG. 3 is a time chart for the slip application steps.

The process of slip application will now be described. The various parts of the tank are subjected at their surfaces to burning with oil and blasting with grit and then are joined together by welding. The slip is passed through a filter of about 40 mesh to eliminate clusters thereof before being introduced into the tank. In introducing the slip into the tank, the tank is placed in a lying position. After closing the feedwater ports 7, 8, hot water outlets 9–11 and electrode mounting openings 12, 13, the interior of the tank was pressurized to 1.2 $kg/cm^2$. Then, as shown in the time chart in FIG. 3, the tank is inclined at an angle of −45° with respect to the vertical (the inclined angle of the tank is taken plus when the flue is disposed in the upper position) and started rotating at 20 rpm. After the lapse of a given time, the rotating tank is inclined at an angle of +45° with respect to the vertical. Rotation of the tank is continued while the tank is in this position, and rotation is terminated 30 seconds after initiation of the rotation. When the tank stops rotating, the tank is arranged such that the feedwater port 7 is directed downwardly. Then the feedwater port 7 is opened, so that the slip collected in the lower portion of the tank can be forcedly drained through the feedwater port 7 by the pneumatic pressure in the upper portion of the tank.

Thereafter exhausting of the tank is performed. The slip has a high viscosity, so that the slip may be collected in a thick layer around the feedwater port 7 without being let out completely. The exhausting step is performed to completely drain the slip from the tank. In effecting exhaust of the slip from the tank, the tank is tilted to let out the collected slip. Since the feedwater port 7 opens at the side of the tank, the tank is first brought to an upright position to drain the slip positioned in the upper portion of the tank through the feedwater port 7, and then the tank is brought to a lying position to drain the slip positioned in the lower portion of the tank through the feedwater port 7. This operation is performed twice.

Figure 4:
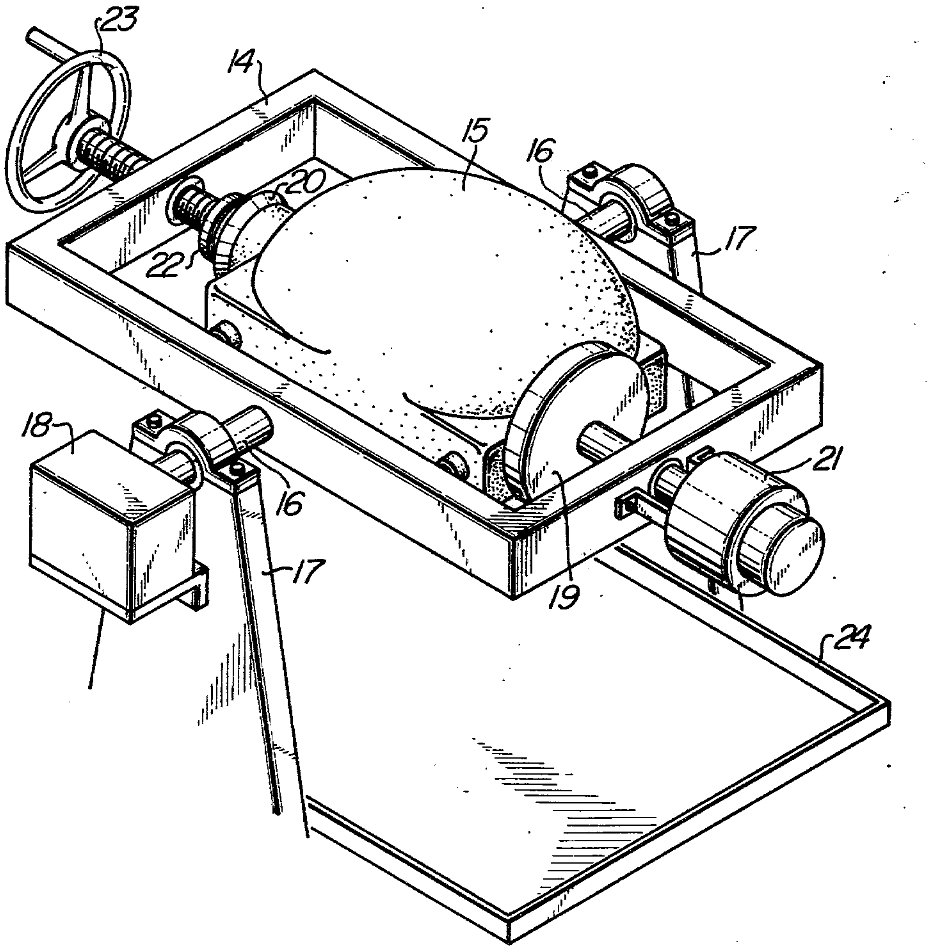
FIG. 4 is a perspective view of a slip applying apparatus adapted to carry the method according to the invention into practice.

An apparatus suitable for rotating and slanting the tank is shown in FIG. 4 wherein 14 designates a frame for supporting a tank 15 supported for rotation through shafts 16 by a support base 17. One shaft 16 is provided with means 18 for causing the frame 14 to incline. The numerals 19 and 20 designate support seats for supporting the tank 15 which are mounted for rotation relative to the frame 14. One support seat 19 is provided with rotation driving means 21, and the other support seat 20 is axially movable through a rotary joint 22. By turning a handle 23, it is possible to move the support seat 20 to mount or remove the tank 15 in the frame 14. The numeral 24 refers to a tray for receiving drained slip.

After the tank has been exhausted, the feedwater port 8, hot water outlets 9–11 and electrode mounting openings 12, 13 are opened to effect drying of the applied slip. Forced drying is adopted to complete drying in a short period of time. Heated air flows are forcedly supplied through the feedwater ports 7 and 8 and exhausted from the hot water outlets 9–11 and electrode mounting openings 12, 13. In performing forced drying, air currents heated at a temperature of 80° C. are first passed for one minute at a rate of 15 m/sec (at the feedwater ports), and air flow heated at temperature of 80° C. are passed for 19 minutes at a rate of about 50 m/sec (about 4 $m^3$/min). By this forced drying, over 80% of the applied slip is dried.

The tank in which slip application has been effected as aforesaid is fed to a baking furnace to be fired therein, after being passed through a drying furnace utilizing hot blast (of a temperature of about 120° C.) supplied from the baking furnace.

Figure 5:
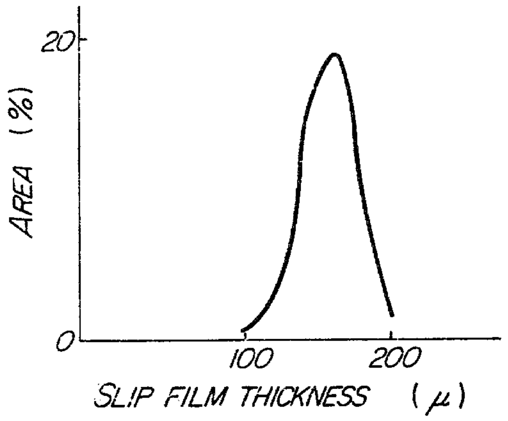
FIG. 5 is a graph showing the distribution of thickness of an enamel coating.

When a tank is supplied with slip and the coat of slip thus formed is fired, the enamel coating has a thickness of about 160$\mu$ on an average. FIG. 5 shows a curve representing a thickness distribution of the coating. It has been found that the surfaces near the slip outlet port tend to have an enamel coating of a larger thickness or over 300$\mu$ because the slip collects therein depending on how tank exhausting is performed. The slip coat applied by the aforementioned method shows no slumping or sagging, and its appearance is similar to that of the enamel coating applied by the spraying method of the prior art. It goes without saying that the slip applying operation should be performed with caution, as is the case with slip application by means of a conventional method, with respect to the joint surfaces of the pipe receiving openings and the tank and other surfaces such as welded surfaces on which the defects of discontinuity of the slip applied surfaces tend to occur. It appears that the method according to the invention leaves something to be desired in preventing discontinuity of the enamel coated surfaces and unevenness of the thickness of the applied enamel, as compared with the spray method. Therefore, it would be advisable to use electrical corrosion preventing method in combination with this method.

The reasons why the aforesaid values are used will now be described.

Figure 6:
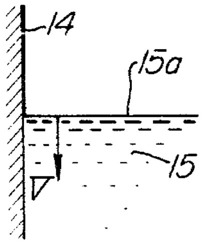
FIG. 6 is a view in explanation of the relationship between the slip applied surface and slip.
Figure 7:
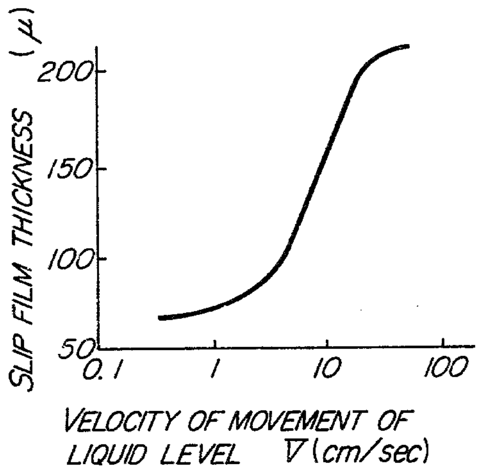
FIG. 7 is a graph showing the relationship between the rate of movement of the liquid level of slip and the thickness of an enamel coating.

With reference to the use of a pneumatic pressure of 1.2 $kg/cm^2$, the pneumatic pressure is used to obtain a desired rate of movement v (downward movement) of a liquid level 15a of slip 15 relative to a slip applied surface 14 as shown in FIG. 6. It is necessary that the desired rate of movement be obtained, even if the liquid level 15a has moved downwardly to a position near the feedwater port 7 when excess slip is drained from the tank. The result of an experiment conducted on the relation between the rate of movement v and the thickness of the coating in $\mu$ is shown in FIG. 7. When the slip used has a specific gravity of 1.76, a viscosity cup time of 4.5 seconds and a particle size of 43.3 g (milling was done in a 7 l pot mill), the rate of movement v should be 20 cm/sec if the desired thickness of an enamel coating is 200$\mu$. Changes in the specific gravity and viscosity of the slip have been found to cause changes mainly in the maximum value of the coating thickness and to cause no appreciable changes in the minimum value thereof. The pneumatic pressure of 1.2 $kg/cm^2$ has been determined for providing an enamel coating of a thickness of about 200$\mu$ in a tank of the construction mentioned above.

The tank is rotated a plurality of times for certain periods of time by changing the position of the tank, because the slip coat has not enough wettability to obtain a desired coating thickness if the tank is rotated only once in the same position.

The amount of slip introduced into a tank and the angle of inclination of the tank while slip application is being performed will now be described. In general, the amount of the slip introduced into the tank is preferably small, when the time required for pouring the slip in the tank and the time required for draining the slip from the tank are taken into consideration. In the embodiment described above, the tank is rotated both in a position in which it is inclined −45° and a position in which it is inclined +45° with respect to the vertical. It should be understood that the amount of the slip introduced into the tank and the angle of inclination of the tank are related to the shape of the tank.

In regard to exhausting of a tank or letting slip completely out of the tank, the angle of inclination of the tank and the number of times of inclination may be determined depending on the shape of the tank and the amount of slip drained in one operation. If the slip outlet port is funnel-shaped and its opening faces downwardly to facilitate draining of the slip, there is no need to perform a tank exhausting operation.

The nature of the slip will now be described. The thickness of an enamel coating provided is greatly influenced by a pickup value. To obtain an enamel coating of a thickness of about 160μ, one has only to use a pickup value of about 10 g/dm$^2$. This pickup value is smaller than that used for a conventional spray method. The slip used in the invention has the same specific value as the slip used in a conventional spray method. The pickup value is defined as the weight of the slip adhering to a stainless steel plate (1.0 t×100 mm×100 mm) when the stainless steel plate is moved upwardly out of a pool of slip at a predetermined speed (about 20 cm/sec).

Slip has a thixotropic property or it becomes fluid when agitated and then sets when left at rest. Thus the slip applied to the interior surfaces of a tank shows such phonomena as slumping and sagging. Accordingly, a slip coat of a uniform thickness cannot be provided even if an attempt is made to provide an enamel coating of a desired thickness by relying on the pickup value. The particle size, rather than the viscosity, of slip exerts greater influences on uniform slip application. Therefore, in the present invention, an attempt has been made to prevent sagging and slumping of applied slip by selecting slip of a suitable particle size.

Slip of various particle sizes has been tested by using thixotropy as a measure of uniform slip application. The following table shows the result of the test.

TABLE

| Particle Size | 5 | 10 | 15 | 20 | 25 | 30 | 35 | 40 | 45 |
|---|---|---|---|---|---|---|---|---|---|
| Thixotropy | X | X | Δ | Δ | O | ◎ | ◎ | ◎ | ◎ |

Note:
Specific gravity is 1.76 (constant).◎ excellent; O good; Δ, fair; and X, poor In the above table, it will be seen that slip of a particle size in the range from 25 to 45 g is suitable, when the fluidity of slip and the smoothness of an enamel coating surface are taken into consideration. It is to be understood that the slip used in the test has been prepared in a 7 l pot mill, and no experiments on the thixotropy of slip of a particle size over 45 g have been conducted. However, it is doubtful if a slip of a particle size of over 50 or 60 g is of any value in providing an enamel coating designed to withstand the effects of hot water. Also, conventional milling is considered to be unsuitable because the specific gravity and particle size become too low in value.

In this specification, the particle size is represented by the weight of remnants washed with water and dried after slip of 100 c.c. is passed through a filter of 40 mesh and then again passed through a filter of 200 mesh. Evaluation of the thixotropic property has been done by moving upwardly a grit steel plate from a pool of slip and by visually inspecting the slumping of the slip applied to the surface of the plate.

From the foregoing, it will be seen that the slip used in this invention is larger in particle size than the slip used in a conventional spray method. It is generally believed that the greater the particle size, the lower is the capability of an enamel coating to withstand the effects of hot water. However, the result of a test shows that the capability of the enamel coating provided by the method according to the invention is similar to that of an enamel coating applied by a conventional method. Assessment of the capability is based on the result of a sample test using a plate of 100 mm×100 mm. No problem has been encountered with respect to the steam solubility specified in CS standards 115-60 in the U.S.A. The bubble structure of the section of an enamel coated surface has been similar to that of an enamel coated surface provided by a conventional method.

The particle size of slip is in inverse proportion to the milling time. Thus, this invention enables productivity to be increased by reducing the milling time.

The step of drying the applied slip by forcedly passing a currents of heated air through the tank will now be described. Forced drying is adopted to effect drying of the applied slip in a short period of time. The tank has two shells with an inner shell being closed at its bottom and a hot water reservoir having openings of a small size for communication with the outside. The tank being of such construction, if the tank is heated from outside as has hitherto been done, an atmosphere of 100% saturated steam of the vaporization temperature of the heated surfaces will be produced, and condensation will be immediately formed on surfaces of the inner cylinder and flue of a temperature which is lower than the temperature of the heated surfaces. The condensation will wet the surfaces, causing the applied slip to flow downwardly. Forced drying of the slip applied surfaces is effected to prevent this accident. Air currents are supplied from left and right sides of the tank and vented from left and right sides thereof, in order to vent saturated steam from various portions of the tank. The temperature of the heated air is related to the amount of supplied air and time.

Air is initially supplied at low speeds in order to prevent the slip on portions of the inner shell facing the air supply ports from being blown away by the jet streams of air. After the slip applied to surfaces of the inner shell is dried and sets, air is supplied at high rate so as to reduce the drying time.

The use of forced drying relying on the supply of air currents facilitates a drying operation even if the tank has a single shell, as is the case with a hot water reservoir tank.

In the aforesaid embodiment, pneumatic pressure is used as means for controlling the rate at which excess slip is drained from the tank. It is to be understood that the tank may be rotated to apply slip to the interior surfaces thereof without pressurizing the interior of the tank, and excess slip may be forcedly drained by means of a suction pump or by connecting the tank to a vacuum chamber, so as to obtain a required speed of downward movement of the slip.

A comparison of the use of pressurized air and the use of a suction pump or a vacuum chamber shows that, since compressed air is generally used in plants for fabricating tanks of this type as drive power, the use of pneumatic pressure is advantageous. Also, the rate at which excess slip is drained can be varied readily by varying the pneumatic pressure. Thus the use of pneumatic pressure will be more convenient. It is to be understood that other gases than air may be used as means for forcedly draining excess slip from the tank.

In the embodiment described above, pressurization of the interior of the tank is effected prior to application of slip to interior surfaces of a tank while the tank is being rotated. It is to be understood that the interior of the tank may be pressurized following slip application by rotation of the tank. If this is the case, care should be exercised so as not to cause the applied slip to fly about by jet steams of supplied air.

The air is preferably non-mist air.

In the aforementioned embodiment, slip application is performed only once. In this case, it is necessary to increase the amount of heat required for firing the applied slip as compared with the amount of heat required for applying two coats of slip.

Also, when two coats of slip are applied by the method according to the invention, it is necessary to pay special attention to the collection of slip in the vicinity of the slip outlet port.

What is claimed is:

1. A method of applying slip to interior surfaces of a closed tank to provide an enamel coating thereon, comprising the steps of:

(a) introducing the slip for forming the enamel coating into the interior of the closed tank in an amount that is larger than that actually required for forming the enamel coating but smaller than the internal volume of the tank, said slip having a particle size, specific gravity and viscosity preselected to provide said enamel coating;

(b) immediately after the introduction of slip into the tank, introducing pressurized air into said closed tank;

(c) applying slip to an interior surface of the tank during rotation of said tank whereby the rate at which the slip flows across the interior surface of the tank being coated results in an enamel coating of a desired thickness; and (d) forcibly draining from the tank that excess slip which has not been applied to the interior surface of the tank by the pressurized gases introduced into said tank, said excess slip being drained from the tank at a rate which results in an enamel coating on an interior surface of the tank of a desired thickness.

2. A method as claimed in claim 1, wherein after the pressurized gases are introduced into the tank, the tank is inclined with one end lower than the other, the tank is then rotated so that the slip is applied to the interior surfaces of the tank at the one end during rotation thereof, the tank is then inclined so that the one end is higher than the other end during further rotation of the tank whereby slip is applied to the other end of said tank, rotation of the tank is then stopped and excess slip is forcibly drained from said tank via an outlet opening, said pressurized gases causing excess slip to drain from the tank at such a rate as to produce an enamel coating of the desired thickness at said other end of the tank.

3. A method as claimed in claim 1, wherein the excess slip is drained from the tank via an outlet port located at an end of the tank.

4. A method as claimed in claim 1, wherein the particle size of said slip is in the range of from 25 to 45 g.

5. A method as claimed in claim 1, wherein the excess slip is drained from the tank after the tank has ceased to be rotated.

6. A method as claimed in claim 1, wherein the tank which has been filled with pressurized gases after the introduction of slip thereinto is rotated about the axis of revolution of the tank as well as about the axis perpendicular to the axis of revolution.

7. A method as claimed is claim 6, wherein slip application is begun when the tank is disposed in such an inclined position that a slip discharge port on one side of the tank is higher in level than the opposite side thereof.

8. A method as claimed in claim 1, wherein after the excess slip has been forcedly drained from the tank, rotation thereof is stopped, and the slip remaining about the discharge port then is drained with the tank disposed in an inclined position.

9. A method as claimed in claim 1, wherein after the excess slip has been drained from the tank, the interior thereof is supplied with hot air flow to cause the slip applied to the interior surfaces of the tank to be dried.

10. A method as claimed in claim 9, wherein said hot air flow is initially supplied at a low velocity of flow and is then supplied at a high velocity of flow after the slip on the slip-coated surfaces facing the air inlet ports is dried and sets.

11. A method as claimed in claim 1 wherein said gases are air drained from the tank by the pressurized air.

12. A method as claimed in claim 1 wherein after the excess slip has been forcibly drained from the tank, hot air is passed through the interior of the tank, said hot air initially being supplied at a low rate until the slip applied to portions of the interior surface of the tank facing the area of air supply is dried and set and thereafter the hot air is supplied at a higher rate to reduce the time required for effecting drying of the applied slip.

13. A method as claimed in claim 1, wherein the slip is introduced into the interior of the closed tank via a port of said tank.

14. A method as claimed in claim 1, wherein said closed tank is equipped with inlet and outlet ports that have diameters that are smaller than the diameter of the tank, the slip being introduced into the tank via one of said ports and the slip being drained from said tank via one of said ports.

15. A method as claimed in claim 1, wherein after the slip is introduced into the closed tank, all ports are closed prior to rotation of said tank.

16. A method as claimed in claim 1, wherein rotation of the tank is stopped after a predetermined period of rotation and then the excess slip is drained from a stationary tank.

* * * * *